United States Patent
Gopalkrishnan et al.

(10) Patent No.: US 6,342,206 B1
(45) Date of Patent: Jan. 29, 2002

(54) AQUEOUS GELS COMPRISING ETHOXYLATED POLYHYDRIC ALCOHOLS

(76) Inventors: Sridhar Gopalkrishnan, 8641 Woodside Dr., Grosse Ile, MI (US) 48138; Richard J. Holland, 19 Pheasant Ct., Flanders, NJ (US) 07826; James S. Dailey, 28594 Chatham, Grosse Ile, MI (US) 48138; Kathleen M. Guiney, 423 Maple St., Wyandotte, MI (US) 48192

( * ) Notice: Subject to any disclaimer, the term of this patent is extended or adjusted under 35 U.S.C. 154(b) by 0 days.

(21) Appl. No.: 09/472,471

(22) Filed: Dec. 27, 1999

(51) Int. Cl.⁷ .............................. A61K 7/16; A61K 7/22
(52) U.S. Cl. ............................................. 424/49; 424/53
(58) Field of Search ....................... 424/49–58

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 2,980,655 A | 4/1961 | Glass et al. |
| 4,276,430 A | 6/1981 | Reller et al. |
| 4,478,853 A * | 10/1984 | Chaussee .................... 424/358 |
| 4,623,537 A * | 11/1986 | Kearns ........................ 424/49 |
| 4,687,663 A | 8/1987 | Schaeffer |
| 4,745,231 A | 5/1988 | Lange et al. |
| 5,059,417 A | 10/1991 | Williams et al. |
| 5,135,748 A * | 8/1992 | Ziegler et al. ............... 424/401 |
| 5,169,624 A * | 12/1992 | Ziegler et al. ............... 424/59 |
| 5,279,816 A | 1/1994 | Church et al. |
| 5,292,527 A | 3/1994 | Konopa |
| 5,380,528 A * | 1/1995 | Alban et al. ................. 424/401 |
| 5,407,668 A | 4/1995 | Kellner |
| 5,420,118 A * | 5/1995 | Alban et al. .................... 514/63 |
| 5,424,070 A | 6/1995 | Kasat et al. |
| 5,665,366 A | 9/1997 | Rawlings et al. |
| 5,690,911 A | 11/1997 | Mirajkar et al. |
| 5,707,635 A * | 1/1998 | Deckner et al. ............ 424/401 |
| 5,858,340 A * | 1/1999 | Briggs et al. ............. 424/70.19 |
| 5,866,527 A * | 2/1999 | Mertens ...................... 510/422 |
| 5,908,612 A * | 6/1999 | Dailey et al. ................. 424/49 |
| 5,911,915 A * | 6/1999 | Fonsny et al. ............... 252/312 |
| 6,037,328 A * | 3/2000 | Hu et al. ...................... 514/23 |
| 6,080,706 A * | 6/2000 | Blanvalet et al. ........... 510/108 |

* cited by examiner

Primary Examiner—Shep K. Rose
(74) Attorney, Agent, or Firm—David T. Banchik, Esq.

(57) ABSTRACT

There is provided according to the present invention an aqueous gel composition, comprising
  a) an ethoxylated polyhydric alcohol which comprises a reaction product of an alcohol having 3 to 6 hydroxy groups with ethylene oxide; and
  b) a gelling agent selected from the group consisting of a polyoxyethylene/polyoxypropylene/polyoxyethylene triblock surfactant having a molecular weight of from 4,000 to 16,000, and wherein the weight of the polyoxyethylene blocks is from 55% to 90% of the weight of the triblock surfactant; a crosslinked polyacrylic thickener; cellulose derivatives; hydrated silicas; and mixtures thereof.

When the gelling agent is the triblock surfactants, the ethoxylated polyhydric alcohol comprises the reaction product of the polyhydric alcohol and up to 5 mole equivalents of ethylene oxide per mole equivalent of hydroxyl group in the alcohol.

19 Claims, No Drawings

AQUEOUS GELS COMPRISING ETHOXYLATED POLYHYDRIC ALCOHOLS

FIELD OF THE INVENTION

The invention relates to ethoxylates of polyhydric alcohols, and their use in dentifrice gels or personal care compositions.

BACKGROUND OF THE INVENTION

The use of ethoxylated polyhydric alcohols, such as glycerol and sorbitol, is known in skin care and pharmaceutical compositions. The use of ethoxylated glycerol in an oral composition at a use level of 0.15%, as part of a sodium lauryl sulfate/nonionic surfactant blend, has also been reported.

The use of high molecular ethylene oxide/propylene oxide triblock surfactants in aqueous gel compositions is well known. See, for example, the discussion in U.S. Pat. No. 5,908,612. With such triblock surfactants, aqueous gel compositions can be readily formed which have desirable viscosity properties over an appropriate temperature range.

It is also known to make aqueous gel compositions from such triblock surfactants in combination with glycerol.

A peroxide gel dentifrice comprising glycerol, a triblock surfactant, and a peroxide material has been reported, as has a mouthwash containing a nonionic surfactant which can be a polyoxyethylene polyoxypropylene block surfactant, a humectant which can be glycerol, and an antibacterial agent.

It is known to use gelling agents with humectants such as glycerol or sorbitol in order to make aqueous toothpastes. Such gelling agents include crosslinked polyacrylic thickeners, cellulose derivatives, and hydrated silicas.

The use of ethoxylated polyhydric alcohols to prepare aqueous dentifrice gels is unknown. Nor have the ethoxylated polyhydric alcohols been used as humectants or as a carrier in toothpaste compositions.

Applicants have surprisingly found that certain ethoxylated polyhydric alcohols having an effective amount of ethoxylation are useful in preparing aqueous dentifrice compositions. Furthermore, the ethoxylated polyhydric alcohols exhibit many advantages over the materials used in the prior art.

Aqueous gel compositions made with polyoxyethylene/polyoxypropylene/polyoxyethylene triblock surfactants are thermally reversible, a property which formulators have taken advantage of to facilitate the processing of such gels. Furthermore, gels formulated with the triblock surfactants show exceptional tolerance toward electrolytes and are stable over wide ranges of pH and temperature.

However, a common limitation with dentifrice gels formulated with copolymers of ethylene oxide and propylene oxide is that due to their thermally reversible gelation properties, the gels can instantly liquefy to a pourable liquid as soon as the temperature falls below the sol-gel transition temperature. Such an event can possibly lead to leakage of fluid from the package. It has been surprisingly discovered that dentifrice compositions containing suitable amounts of ethoxylated polyhydric alcohols protect the dentifrice gel composition from sudden loss of viscosity at lower temperatures.

Another advantage of the ethoxylated polyhydric alcohols of the present invention is that they are good solvents for a variety of flavor oils.

SUMMARY OF THE INVENTION

There is provided according to the present invention an aqueous gel composition, comprising a) an ethoxylated polyhydric alcohol which comprises a reaction product of an alcohol having 3 to 6 hydroxy groups with ethylene oxide; and b) a gelling agent selected from the group consisting of a polyoxyethylene/polyoxypropylene/polyoxyethylene triblock surfactant having a molecular weight of from 4,000 to 16,000, and wherein the weight of the polyoxyethylene blocks is from 55% to 90% of the weight of the triblock surfactant; a crosslinked polyacrylic thickener; cellulose derivatives; hydrated silicas; and mixtures thereof.

In one embodiment, the invention is an aqueous gel composition comprising an ethoxylated polyhydric alcohol, a gelling agent and water. The ethoxylated polyhydric alcohol comprises the reaction product of an alcohol having 3 to 6 hydroxyl groups with ethylene oxide, preferably such that up to 5 mole equivalents of ethylene oxide are reacted per mole equivalent of hydroxyl group. The gelling agent is selected from the group consisting of polyoxyethylene/polyoxypropylene/ polyoxyethylene triblock surfactants, crosslinked polyacrylic thickeners, cellulose derivatives, and hydrated silicas. When the gelling agent is the triblock surfactants, the ethoxylated polyhydric alcohol comprises the reaction product of the polyhydric alcohol and up to 5 mole equivalents of ethylene oxide per mole equivalent of hydroxyl group in the alcohol.

DETAILED DESCRIPTION OF A PREFERRED EMBODIMENT

The ethoxylated polyhydric alcohols of the present invention can be prepared by means well known in the art by reacting a polyhydric alcohol with appropriate amounts of ethylene oxide in the presence of an alkaline catalyst. The resulting polyether may be optionally neutralized with neutralization acids well known in the art. See, for example, *Block & Graft Copolymerization*, Volume 2, Chapter 1, edited by R. J. Ceresa (Wiley, 1981), hereby incorporated by reference.

Polyhydric alcohols useful for making the ethoxylated polyhydric alcohols of the present invention are generally those that have from 3 to 6 hydroxyl groups. Examples of polyhydric alcohols include, but are not limited to, glycerol, trimethylolpropane, 1,2,6-hexanetriol, ditrimethylolpropane, pentaerythritol, glucose, and sorbitol. The ethoxylated polyhydric alcohol is thus the reaction product of an alcohol having 3 to 6 hydroxyl groups and an appropriate amount of ethylene oxide.

As shown in Table 1, the ethoxylated polyhydric alcohols of the invention are good solvents for flavoring oils. In Table 1, it can be seen that 0.2% solutions of the flavoring oils in the polyhydric alcohols (exemplified by a glycerol 12 mole ethoxylate) give clear solutions while the solutions in glycerol are hazy.

TABLE 1

Solutions of 0.2% flavor oils in ethoxylated polyhydric alcohol

| PRODUCT | EUCA-LYP-TUS OIL | CAM-PHOR | METHYL SALICY-LATE | MEN-THOL | THYMOL |
|---|---|---|---|---|---|
| GLYCEROL | Hazy | Hazy | Hazy | Hazy | Hazy |
| GLYCEROL + 12 eo | Clear | Clear | Clear | Clear | Clear |

Table 2 presents a comparison of the physical properties of glycerin and three different ethoxylated polyhydric alcohols (represented by ethoxylated glycerol with levels of ethoxylation from 10 to 20). It is seen that whereas glycerol has a sweet taste, the glycerol ethoxylates are essentially tasteless. That is, the ethoxylated polyhydric alcohols of the present invention do not have the sweet taste of glycerin. This may provide a benefit to formulators who do not prefer the sweet taste of glycerin. Formulators using glycerin in such compositions often have to rely upon expensive flavoring agents to mask the sweet taste imparted by glycerin. Since glycerol ethoxylates are essentially tasteless, the use of masking agents in dentifrice compositions can be minimized. Alternatively, the lack of sweetness may be compensated for, if desired, by adding sweeteners to compositions of the invention containing ethoxylated polyhydric alcohols.

TABLE 2

| PRODUCT | TASTE | POUR POINT |
| --- | --- | --- |
| GLYCEROL | SWEET | 17° C. |
| GLYCEROL-10 MOLE EO | TASTELESS | −39° C. |
| GLYCEROL-12 MOLE EO | TASTELESS | not determined. |
| GLYCEROL-20 MOLE EO | TASTELESS | −5° C. |

The ethoxylated polyhydric alcohols of the current invention find utility in aqueous based dentifrice compositions in two ways, which will be described below.

The first is as a component of an aqueous gel composition comprising a particular class of polyoxyethylene/polyoxypropylene/polyoxyethylene triblock surfactant. The ethoxylated polyhydric alcohols of the invention can be used to replace partially or completely the known compounds such as glycerol which have been used in such formulations up to now. For this application, the level of ethoxylation on the ethoxylated polyhydric alcohol can have an important impact on the gelling properties.

The second is as a humectant or carrier in aqueous based toothpaste compositions comprising one or more known thickening agents such as crosslinked polyacrylic thickeners, cellulose derivatives, and hydrated silicas. The ethoxylated polyhydric alcohol can partially or completely replace commonly used humectants such as glycerol, sorbitol, propylene glycol, and polyethylene glycol. Here, the level of ethoxylation is not very critical to the gelling or thickening properties. However, if necessary, ethoxylated polyhydric alcohols with relatively lower levels of ethoxylation may be used so that desired humectancy properties can be achieved.

There is provided according to the present invention an aqueous gel composition, comprising
  a) an ethoxylated polyhydric alcohol which is the reaction product of an alcohol having 3 to 6 hydroxy groups with ethylene oxide; and
  b) a gelling agent selected from the group consisting of polyoxyethylene/polyoxypropylene/polyoxyethylene triblock surfactants having a molecular weight of from 4,000 to 16,000, and wherein the weight of the polyoxyethylene blocks is from 55% to 90% of the weight of the triblock surfactant; crosslinked polyacrylic thickeners; cellulose derivatives; and hydrated silicas.

A preferred gelling agent is the polyoxyethylene/polyoxypropylene/ polyoxyethylene triblock surfactants. The triblock surfactant is preferably present at a level of 16 to 40 percent by weight of the total composition, more preferably from 16 to 25 percent by weight. Such triblock gelling agents are well known in the art. The preferred gelling agents contain an internal block of polyoxypropylene and two external blocks of polyoxyethylene. The triblock gelling agents generally have a molecular weight of 4000 or greater, and the molecular weight of the polyoxyethylene blocks is from about 55 to about 90% of the molecular weight of the triblock surfactant. The molecular weight of the triblock surfactant can be up to about 16,000. Preferred triblock gelling agents have a molecular weight greater than about 8000, and a polyoxyethylene content of about 60–85%. Suitable gelling agents of this class are commercially available under the PLURONIC® line of surfactants sold by BASF Corporation, including in particular PLURONIC® F 127, PLURONIC® F 108, and PLURONIC® F 98.

Alternatively, crosslinked polyacrylic thickeners can be used as the gelling agent. Examples of these crosslinked polyacrylic thickeners are the Carbopol products of B. F. Goodrich, such as are described in U.S. Pat. Nos. 2,798,053; 2,923,692; and 2,980,655; the disclosures of which are hereby incorporated by reference. Preferred crosslinked polyacrylic thickeners also include water dispersible copolymers of acrylic acid crosslinked with about 0.75 to about 1.5% of polyallyl sucrose and neutralized with triethanolamnine, NaOH or another neutralizing agent, as taught in U.S. Pat. No. 3,499,844, the disclosure of which is hereby incorporated by reference. Commercially available crosslinked polyacrylic thickeners include Carbopol® 940, Carbopol® 934, and Ultrez® 10, products of B. F. Goodrich.

Such thickeners are essentially colloidally water insoluble acidic carboxylic polymers of acrylic acid crosslinked with about 0.75 to about 2 percent of a crosslinking agent comprising polyallyl sucrose or polyallyl pentaerythritol. They are present in the aqueous gel composition of the present invention at a level of about 0.1 to about 10 percent, preferably about 0.5 to about 5 percent, and most preferably about 0.5 to about 2 percent, based on the total weight of the composition.

Another preferred class of gelling agent is the cellulose derivatives. These include carboxymethyl cellulose, hydroxyethyl cellulose, hydroxyethyl propylcellulose, hydroxybutyl methylcellulose, hydroxypropyl methylcellulose, and sodium carboxymethyl cellulose. They are present in the aqueous gel composition of the present invention at a level of about 0.1 to 3%, preferably about 0.5 to 2%, and more preferably at about 1%. Commercially available examples of suitable cellulose derivatives include Aqualon® CMC-7MXF and CMC-9M8XF from Aqualon, a division of Hercules.

The hydrated silicas useful in the invention are in general precipitated silica thickeners. As such, they comprise a precipitate obtained when a sodium silicate solution is acidified. A useful precipitated silica thickener is commercially available under the tradename Sident® 22 S, a product of Degussa.

In water-containing toothpaste formulations, the hydrated silicas are advantageously used together with low-, medium-, or high structured silica abrasives. The hydrated silicas can also be combined with other thickeners such as carboxymethyl cellulose. The hydrated silicas are used in an effective amount, which is typically between about 2% and about 15% by weight, based on the total weight of the composition.

The cellulose derivatives and hydrated silicas useful in the gel compositions of the current invention are further described in *Chemistry & Technology of the Cosmetics & Toiletries Industry*, by D. F. Williams & W. H. Schmitt, pages 246–260, the disclosure of which is hereby incorporated by reference.

Aqueous Gel Compositions with Triblock Surfactants

In general, ethoxylated polyhydric alcohols can be used to make the aqueous gels of the present invention. Where the gelling agent is the ethylene oxide/propylene oxide triblock surfactant, it has been found that the level of ethoxylation of the polyhydric alcohol can critically impact the gel properties of the composition. In such a case, ethoxylated polyhydric alcohols are used which comprise the reaction product of an alcohol having 3 to 6 hydroxyl groups, and an amount of ethylene oxide such that, on average, up to 5 mole equivalents of ethylene oxide are reacted per mole equivalent hydroxyl on the polyhydric alcohol. For example, if the polyhydric alcohol is glycerol having 3 hydroxyl groups, the amount of ethylene oxide used can be up to 15 moles of ethylene oxide per mole of glycerol, so that an average 5 moles of ethylene oxide react with each of the three mole equivalents of hydroxyl group on the glycerol. Likewise, for sorbitol, a polyhydric alcohol having 6 hydroxyl groups, up to 30 moles of ethylene oxide are reacted with sorbitol so that up to 5 mole equivalents of ethylene oxide are reacted per mole equivalent of hydroxyl group on the sorbitol.

Thus, when the gelling agent is the triblock surfactant, a preferred ethoxylated polyhydric alcohol is ethoxylated glycerol having an average of up to about 15 units of ethylene oxide per glycerol molecule. Preferably, the ethoxylated glycerol will have an average of up to about 12 units of ethylene oxide per glycerol molecule. Another preferred ethoxylated polyhydric alcohol is ethoxylated sorbitol having an average of up to about 30 units of ethylene oxide per sorbitol molecule.

To form the aqueous gels of the present invention where the gelling agent is a triblock surfactant, the ethoxylated polyhydric alcohol is generally used at a level of about 1 to about 60%. It is preferably used at a level of about 10 to about 60% by weight of the total composition. More preferably, 15 to 50 percent and most preferably, 20 to 40 percent by weight is used. The aqueous gels of the invention can further comprise conventional humectants such as glycerol, sorbitol, propylene glycol, and liquid polyethylene glycols.

Where the ethoxylated polyhydric alcohols are present at less than about 10%, it will generally be desirable to add one or more of the conventional humectants to the composition in such an amount that the total amount of ethoxylated polyhydric alcohol plus conventional humectant is at least about 10% by weight.

The aqueous gel compositions may advantageously further comprise a peroxygen compound. Such peroxygen compounds are well known as ingredients of dentifrice compositions and include compounds that can readily give off oxygen as the decomposition product. Such compounds include, but are not limited to, hydrogen peroxide and its alkali metal and alkaline earth salts, urea peroxide, salts of percarbonates, perborates, perphosphates, persilicates, and organic peroxy acids such as peroxyacetic acid. They can be used at any effective level. Typically, levels of 0.1% to about 6% are useful, with a level of 1 to about 4% being preferred. The most preferred range is from about 1 to about 3% by weight of the composition.

The aqueous gel compositions may also advantageously further comprise a flavor oil. Suitable flavoring oils include but are not limited to oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. A flavor system is generally used in the compositions at levels of from about 0.001 percent to about 5 percent, by weight of the composition.

The aqueous gel compositions further comprise water at an amount suitable such that the levels of the ingredients are as stated above.

Suitable gel compositions comprising the ethoxylated polyhydric alcohols and the triblock surfactants of the present invention have significant gel strengths at low temperatures as well as adequate gel strengths at higher temperatures. The simplest measure of gel strength is the viscosity of the gel composition, measured in centipoise using a Brookfield HBDY-III Cone/Plate Viscometer equipped with Spindle 51. All rheology measurements were made at the designated temperature using a shear rate of 38.4 reciprocal seconds. For the purposes of the invention, the gel composition should have a viscosity of at least about 3000 centipoise over the temperature range of interest. Typically, below a certain temperature, which is characteristic of a gel composition system, the composition will exhibit a viscosity significantly lower than that which the composition has above that certain temperature. This temperature is called the sol-gel transition temperature. Depending upon the application, it may be desirable to formulate a gel with significant viscosity at low temperatures, for example, at 10° C., or more preferably, at 0° C., or even lower. As seen in the Examples, it is possible with the compositions of the current invention to formulate gels that have significant gel strengths at a temperature of −20° C. or lower.

Likewise, there is an upper temperature, characteristic of the gel composition system, above which the composition no longer exists as a gel but has lower viscosity. Again, depending upon the application, it may be desirable to formulate gel compositions where this transition temperature is at a relatively higher level. It can be seen in the Examples that it is possible to formulate gel compositions using the ethoxylated polyhydric alcohols and the triblock surfactants of the present invention that have gel-like viscosities at 60° C. and greater.

It is generally desirable that the lower sol-gel temperature be no higher than about 10° C. and that the higher transition temperature be no lower than about 40° C. It is more preferable that the higher temperature transition occur at about 50° C. or higher, and more preferred that the higher temperature transition be 60° or higher.

Dentifrice gels of the present invention can be prepared by adding the ethoxylated polyhydric alcohol and optional ingredients such as humectants, hydrogen peroxide, flavor and dye to water. After all of the ingredients have dissolved, the triblock surfactant gelling agent is added and the mixture is stirred slowly to disperse the gelling agent. The composition is then stored at −20° C., and the mixture is periodically stirred to facilitate hydration of the gelling agent. In a plant this is accomplished by performing the mixing and hydration in a reactor equipped with refrigeration means for holding the temperature below the sol-gel transition temperature of the gel composition.

After the mixing step noted above, the composition can contain significant amounts of entrapped air. Where desired, de-aeration is accomplished by known techniques. For example, the mixture can be held in the reactor below the sol-gel transition point so that the viscosity is below about 3000 centipoise. A vacuum may then be applied to the mixture for a time sufficient to remove entrained air bubbles. The gel composition may also be centrifuged to remove any entrapped air.

A non-limiting example of a typical non-abrasive, peroxide-based gel dentifrice composition comprising a polyoxyethylene/polyoxypropylene/polyoxyethylene triblock polymer as the gelling agent and an ethoxylated adduct of glycerol is shown below. All percentages are by weight of the total composition.

| | |
|---|---|
| EO/PO/EO Triblock Polymer (Pluronic ® F-127) | 20% |
| Ethoxylated Glycerol Adduct (10 moles of EO) | 20% |
| Hydrogen Peroxide | 1.5% |
| Flavor | 0.2% |
| Detergent | 1.5% |
| Purified Water | Balance to 100% |

Additional ingredients such as buffering agents or neutralizing agents that are typically used to adjust the pH or improve the stability of the peroxide in the composition can also be added in minor amounts to the above aqueous dentifrice compositions. Optionally, the compositions can contain minor amounts of chelating agents such as ethylenediamine tetracetic acid or its variants or mixtures thereof, to help prevent the premature decomposition of the peroxygen compound in the composition. Also, with certain gel compositions, it may be desirable to incorporate common humectants such as glycerol or sorbitol to further expand the stability of the gel at temperatures above 60° C. The therapeutic benefits of using such aqueous gel composition as dentifrices can be substantially enhanced by using a combination of the above dentifrice gels along with a typically high abrasive dentifrice composition described below:

| | |
|---|---|
| Dentifrice Carrier | 25–55% |
| Fluoride Salts | 0.1–0.9% |
| Abrasive (sodium bicarbonate, dicalcium phosphate) | 20–60% |
| Thickening Agent | 0–5% |
| Flavor | 0.1–0.9% |
| Foam Agent | 0.5–2% |
| Misc. Additives, Sweeteners, Fluoridating Agent, Foam Boosters | 0.3–3.5% |
| Water | As Needed |

Aqueous gel compositions with other gelling agents

Where the gelling agent is selected from the group consisting of crosslinked polyacrylic thickeners, cellulose derivatives, and hydrated silicas, it has been found that the level of ethoxylation of the ethoxylated polyhydric alcohol is not as critical as it is where the gelling agent is the triblock surfactant. Thus the ethoxylated polyhydric alcohol can be the reaction product of an alcohol having 3 to 6 hydroxyl groups with ethylene oxide up to a molecular weight of about 10,000 or greater. Preferably the molecular weight will be less than about 4,000. Preferred ethoxylated polyhydric alcohols are those with up to about 100 moles of ethylene oxide added per mole of the polyhydric alcohol, more preferred is less than about 50–70 moles of ethylene oxide per mole of the polyhydric alcohol.

On prolonged exposure, dentifrice compositions that contain water tend to lose moisture and gradually harden, eventually losing their toothpaste-like consistency. To prevent this, humectants, such as glycerin or low molecular weight polyethylene glycols, have often been used to restore the moisture balance in the toothpaste composition. It has been found that polyhydric alcohols with a suitable level of ethoxylation are suitable for use as humectants in dentifrice compositions and can advantageously replace in whole or in part the prior art humectants.

Thus, where relatively greater humectancy properties are required, ethoxylated polyhydric alcohols with a relatively lower level of ethoxylation are more suitable for use. As an example, it has been found that glycerol ethoxylates having a level of ethoxylation below about 15 in general have adequate humectancy. More preferably, for greater humectancy a level of ethoxylation less than or equal to about 10 is preferred. Level of ethoxylation here refers to the total number of units of ethylene oxide which is reacted onto the starting polyhydric alcohol. To further illustrate, if it is said that the level of ethoxylation of glycerol is about 20, it means that one is speaking of an ethoxylated glycerol having about 20 units of ethylene oxide per glycerol molecule.

To form the aqueous gels of the present invention wherein the gelling agent is selected from the group consisting of crosslinked polyacrylic thickeners, cellulose derivatives, and hydrated silicas, the ethoxylated polyhydric alcohol is generally used at a level of about 1 to about 60%. It is preferably used at a level of about 10 to about 60% by weight of the total composition. The aqueous gels of the invention can further comprise conventional humectants such as glycerol, sorbitol, propylene glycol, and liquid polyethylene glycols.

Where the ethoxylated polyhydric alcohols are present at less than about 10%, it will generally be desirable to add one or more of the conventional humectants to the composition in such an amount that the total amount of ethoxylated polyhydric alcohol plus conventional humectant is at least about 10% by weight.

It was noted above that the ethoxylated polyhydric alcohols of the invention are better solvents for various flavor oils than are conventional humectants such as glycerol. Thus the use of ethoxylated polyhydric alcohols in dentifrice compositions improves the dispersal and solubilization of flavor oils in such compositions.

Compositions comprising ethoxylated polyhydric alcohols and a gelling agent selected from the group consisting of crosslinked polyacrylic thickeners, cellulose derivatives, and hydrated silicas are typically formulated with conventional additives to produce aqueous based dentifrice compositions. A typical toothpaste would contain, in addition to the ethoxylated polyhydric alcohol and gelling agent, other additives such as

| | |
|---|---|
| Fluoride Salts | 0.1–0.9% |
| Abrasive | 20–60% |
| Baking Soda | 0–10% |
| Thickening Agent | 0–5% |
| Flavor oil | 0.1–5% |
| Foam Agent | 0.5–2% |
| Misc. Additives, Sweeteners, Foam Boosters | 0.3–3.5% |
| Water | As Needed |

The flavor can be one or a mixture of the flavor oils described above.

The fluoride salts are those that are capable of providing free fluoride ions. Preferred salts, which are sources of fluoride ions, include sodium fluoride, stannous fluoride, indium fluoride, potassium fluoride, and sodium monofluorophosphate. Sodium fluoride and stannous fluoride are preferred. Such fluoride ion sources and others are disclosed in U.S. Pat. No. 2,946,725 and U.S. Pat. No. 3,678,154, the disclosures of which are hereby incorporated by reference.

The fluoride ion source should be capable of providing from about 50 ppm to about 3500 ppm, preferably from about 500 ppm to about 3000 ppm, of free fluoride ions.

The abrasive polishing material contemplated for use in the compositions of the present invention can be any material that does not excessively abrade dentine. Typical abrasive polishing materials include carbonates. They also include silicas, including gels and precipitates, aluminas, phosphates including orthophosphates, polymetaphosphates, and insoluble pyrophosphates, and mixtures thereof. The abrasive can be precipitated silica or silica gels, such as the silica xerogels described in U.S. Pat. Nos. 3,538,230 and 3,862,307, the disclosures of which are hereby incorporated by reference.

Suitable thickeners include Irish moss, gum tragacanth, starch, hydroxyethyl propylcellulose, hydroxybutyl methylcellulose, hydroxypropyl methylcellulose, hydroxyethyl cellulose, sodium carboxymethyl cellulose, poly (methyl vinyl ether/maleic anhydride) available, for example, as Gantrez® AN 139 of GAF Corporation and carboxylvinyl polymer, for example, available as Carbopol® 934 or Carbopol® 941 from B. F. Goodrich.

Useful foam agents in the dentifrice compositions of the current invention include surfactants selected from anionic, cationic, nonionic and amphoteric surfactants. Particularly preferred are anionic surfactants such as sodium lauryl sulfate, sodium lauroyl sarcosinate, sodium lauryl ether sulfates, sodium alkyl glycerol ether sulfonate, and alkyl benzene sulfonate. Solid block copolymers of polyoxyethylene and polyoxypropylene can be used to provide a further boost in the foaming performance of the dentifrice composition. Further small amounts of cationic surfactants, having a quaternary nitrogen, can also be used. Examples of such surfactants are the betaines, such as cocoamidopropyl betaine. Such foam agents are typically present at about 0.5 to about 2 percent by weight of the total composition.

Sweetening agents can also be added to dentifrice compositions of the instant invention. These include saccharin, dextrose, sucrose, lactose, maltose, levulose, aspartame, sodium cyclamate, D-tryptophan, dihydrochalcones, acesulfame, and mixtures thereof Various coloring agents may also be incorporated in the present invention. Sweetening agents and coloring agents are generally used in dentifrice compositions at levels of from about 0.005 percent to about 5 percent by weight of the composition.

EXAMPLES 1–4

Example 1 gives a typical formulation and Example 2 gives a specific formula for an aqueous gel dentifrice composition comprising an ethoxylated polyhydric alcohol of the invention and an EO/PO/EO triblock gelling agent. Example 3 gives a typical formulation and Example 4 gives a specific formula for an aqueous gel dentifrice of the invention comprising an ethoxylated polyhydric alcohol and a crosslinked polyacrylic gelling agent.

|  | 1 | 2 | 3 | 4 |
|---|---|---|---|---|
| EO/PO/EO triblock polymer (Pluronic ® F 127) | 20–30 | 20 | — | — |
| Crosslinked polyacrylic thickener (Carbopol Ultrex 10) | — | — | 0.2–2 | 1 |
| Ethoxylated glycerol (10 moles of EO) | 20–50 | 40 | 20–40 | 20 |
| Hydrogen peroxide | 1–1.5 | 1.5 | 0–2 | 1.5 |
| Flavoring oil | 0.1–0.2 | — | 0.1–0.2 | — |
| Dye (FDC Blue 1) | 0.001–0.005% | — | 0.001–0.005% | — |
| Water | Balance to 100 | 38.45 | Balance to 100 | 77.5 |

EXAMPLES 5–13

Examples 6–10 illustrate aqueous gel compositions where the gelling agent is the triblock surfactant (exemplified by Pluronic® F127 surfactant). In all examples, water is present at a level such that the total weight of the composition is 100. The viscosity values are given in centipoise, measured by Brookfield spindle 51 at 38.4 $S^{-1}$. The critical nature of the level of ethoxylation is seen by comparing examples 8 and 9. In example 9, a glycerol 12 mole ethoxylate is used to prepare a useful gel composition over the temperature range of 10–60 ° C. However, in example 8, it is seen that an ethoxylated glycerol having 20 moles of ethylene oxide does not give a gel composition having sufficient viscosity over the same temperature to be useful as an aqueous gel dentifrice.

Example 11 shows that sorbitol (here used as the commercially available 70% sorbitol/30% water mixture) is not effective at forming aqueous gels with the nonionic triblock surfactant. However, Example 7 shows that when the sorbitol is ethoxylated to a level of 5 moles of ethylene oxide per mole of sorbitol, a gel results having very useful viscosity properties over the temperature range of 10–60° C. Example 12 shows that sorbitol +40 moles of ethylene oxide, outside the range of the invention, does not produce a gel in combination with the nonionic triblock surfactant.

Example 13 shows a gel composition of the present invention having sufficient viscosity (i.e., greater than 3000 cps) over the temperature range of −20° C. to 60° C. As noted, the composition of Example 13 additionally contained 1.5% by weight hydrogen peroxide.

|  | 5 | 6 | 7 | 8 | 9 | 10 | 11 | 12 | 13ᶜ |
|---|---|---|---|---|---|---|---|---|---|
| Pluronic ® F127 | 20 | 20 | 20 | 20 | 20 | 20 | 20 | 20 | 20 |
| Glycerol | 20 |  |  |  |  |  |  |  |  |
| Sorbitol |  |  |  |  |  |  | 25 |  |  |
| Sorbitol + 5 mol EO |  |  | 25 |  |  |  |  |  |  |
| Sorbitol + 15 mol EO |  | 25 |  |  |  |  |  |  |  |
| Sorbitol + 40 mol EO |  |  |  |  |  |  |  | 25 |  |
| Glycerol + 20 mol EO |  |  |  | 20 |  |  |  |  |  |
| Glycerol + 12 mol EO |  |  |  |  | 20 |  |  |  |  |

-continued

|  | 5 | 6 | 7 | 8 | 9 | 10 | 11 | 12 | 13[c] |
|---|---|---|---|---|---|---|---|---|---|
| Glycerol + 10 mol EO |  |  |  |  |  | 20 |  |  | 40 |
| Viscosity at 60° C. | 9667 | 6717 | 8970 | [a] | 7209 | 9708 | [b] | No gel | 4710 |
| Viscosity at 50° C. | 10527 | 7782 | 10604 |  | 7414 | 10527 |  | No gel | 5734 |
| Viscosity at 20° C. | 11100 | 7700 | 12698 | 415 | 8297 | 11018 | 1426 | No gel | 6717 |
| Viscosity at 10° C. | 8561 | 8110 | 11796 | 427 | 5530 | 8356 | 2508 | No gel | 7455 |
| Viscosity at −10° C. |  |  |  |  |  |  |  | No gel | 8806 |
| Viscosity at −20° C. |  |  |  |  |  |  |  | No gel | 7864 |

[a]not measured, because at 20° C. (room temperature), there was no gel, and it was not expected that it would gel at higher temps.
[b]not measured, because obviously <1426 as at lower temps.
[c]the composition contained in addition 1.5% by weight hydrogen peroxide.

What is claimed is:

1. An aqueous gel composition comprising:
   a) from 15 to 50% by weight of an ethoxylated polyhydric alcohol, which consists essentially of a reaction product of an alcohol having 3 to 6 hydroxyl groups and an amount of ethylene oxide such that up to 5 mole equivalents of ethylene oxide are reacted per mole equivalent of hydroxyl group;
   b) from 16 to 40% by weight of a polyoxyethylene/ polyoxypropylene/ polyoxyethylene triblock surfactant having a molecular weight of from 4,000 to 16,000, and wherein the weight of the polyoxyethylene blocks is from 55% to 90% of the weight of the triblock surfactant; and
   c) water.

2. A gel composition according to claim 1, wherein said ethoxylated polyhydric alcohol comprises an ethoxylated glycerol having an average of up to 15 units of ethylene oxide per glycerol molecule.

3. A gel composition according to claim 1, wherein the ethoxylated polyhydric alcohol comprises ethoxylated sorbitol having an average of up to about 30 units of ethylene oxide per sorbitol molecule.

4. A gel composition according to claim 1, further comprising a peroxygen compound.

5. A gel composition according to claim 1, further comprising a flavor oil.

6. A gel composition according to claim 1, wherein the ethoxylated polyhydric alcohol comprises ethoxylated glycerol having an average of up to 12 units of ethylene oxide per molecule of glycerol.

7. A gel composition according to claim 1 wherein the ethoxylated polyhydric alcohol comprises an ethoxylated glycerol having an average of about 10 units of ethylene oxide per molecule of glycerol, and the triblock surfactant has a molecular weight of about 4000 to 16000, and a percent by content of polyoxyethylene of about 55 to 90 percent.

8. A gel composition according to claim 1, further comprising one or more humectants selected from the group consisting of glycerol, sorbitol, propylene glycol, and polyethylene glycol.

9. A gel composition for use in aqueous dentifrice compositions, comprising
   a) an ethoxylated polyhydric alcohol comprising a reaction product of an alcohol having 3 to 6 hydroxyl groups and ethylene oxide; and
   b) a gelling agent selected from the group consisting of polyoxyethylene/polyoxypropylene/polyoxyethylene triblock surfactants having a molecular weight of from 4,000 to 16,000, and wherein the weight of the polyoxyethylene blocks is from 55% to 90% of the weight of the triblock surfactant; crosslinked polyacrylic thickeners; cellulose derivatives; hydrated silicas; and mixtures thereof.

10. A gel composition according to claim 9, wherein said ethoxylated polyhydric alcohol comprises ethoxylated glycerol having up to about 100 units of ethylene oxide per glycerol molecule.

11. A gel composition according to claim 9, wherein the ethoxylated glycerol comprises glycerol with less than or about 15 units of ethylene oxide per molecule of glycerol.

12. A gel composition according to claim 11, wherein the ethoxylated glycerol comprises glycerol with less than or about 10 units of ethylene oxide per molecule of glycerol.

13. A gel composition according to claim 9, comprising from about 10% to about 60% by weight of said ethoxylated polyhydric alcohol, and wherein said gelling agent comprises about 0.1% to about 10% of a crosslinked polyacrylic thickener.

14. A gel composition according to claim 13, further comprising one or more humectants selected from the group consisting of glycerol, sorbitol, propylene glycol, and polyethylene glycol.

15. A gel composition according to claim 9, comprising from about 10% to about 60% by weight of said ethoxylated polyhydric alcohol, and wherein said gelling agent comprises about 0.1% to about 3% of a cellulose derivative.

16. A gel composition according to claim 15, further comprising one or more humectants selected from the group consisting of glycerol, sorbitol, propylene glycol, and polyethylene glycol.

17. A gel composition according to claim 9, comprising from about 10% to about 60% by weight of said ethoxylated polyhydric alcohol, and wherein said gelling agent comprises about 2% to about 15% of a hydrated silica.

18. A gel composition according to claim 17, further comprising one or more humectants selected from the group consisting of glycerol, sorbitol, propylene glycol, and polyethylene glycol.

19. A gel composition according to claim 9, further comprising a flavor oil.

* * * * *